United States Patent [19]
Someya et al.

[11] Patent Number: 6,013,825
[45] Date of Patent: *Jan. 11, 2000

[54] PROCESS FOR PRODUCING UNSATURATED NITRILE

[75] Inventors: Ken Someya; Hideo Midorikawa, both of Kurashiki, Japan

[73] Assignee: Asahi Kasei Kogyo Kabushiki Kaisha, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/875,898

[22] PCT Filed: Jan. 26, 1996

[86] PCT No.: PCT/JP96/00148

§ 371 Date: Sep. 30, 1997

§ 102(e) Date: Sep. 30, 1997

[87] PCT Pub. No.: WO96/23766

PCT Pub. Date: Aug. 8, 1996

[30] Foreign Application Priority Data

Jan. 31, 1995 [JP] Japan ................................. 7-032865

[51] Int. Cl.[7] ................................................ C07C 253/00
[52] U.S. Cl. ............................................................ 558/324
[58] Field of Search ............................................... 558/324

[56] References Cited

U.S. PATENT DOCUMENTS

| | | | |
|---|---|---|---|
| 3,649,179 | 3/1972 | Ikeda et al. | 23/119 |
| 4,212,766 | 7/1980 | Brazdil et al. | 252/432 |
| 5,258,543 | 11/1993 | Suresh et al. | 558/325 |
| 5,288,473 | 2/1994 | Shaw et al. | 423/237 |
| 5,457,223 | 10/1995 | Shaw et al. | 558/319 |

FOREIGN PATENT DOCUMENTS

| | | |
|---|---|---|
| 40-6451 | 3/1965 | Japan . |
| 44-15645 | 7/1969 | Japan . |
| 45-2371 | 1/1970 | Japan . |
| 45-33538 | 10/1970 | Japan . |
| 47-6608 | 2/1972 | Japan . |
| 47-32968 | 8/1972 | Japan . |
| 48-34824 | 5/1973 | Japan . |
| 48-61425 | 8/1973 | Japan . |
| 48-72122 | 9/1973 | Japan . |
| 49-25560 | 7/1974 | Japan . |
| 49-93316 | 9/1974 | Japan . |
| 49-36690 | 10/1974 | Japan . |
| 51-3131 | 1/1976 | Japan . |
| 51-49149 | 12/1976 | Japan . |
| 52-4500 | 1/1977 | Japan . |
| 52-32893 | 3/1977 | Japan . |
| 53-18014 | 6/1978 | Japan . |
| 2-62-46538 | 10/1987 | Japan . |

*Primary Examiner*—Joseph K. McKane
*Assistant Examiner*—Joseph Murray
*Attorney, Agent, or Firm*—Pennie & Edmonds LLP

[57] ABSTRACT

The present invention is a process for producing an unsaturated nitrile such as acrylonitrile or methacrylonitrile by ammoxidation of an organic compound such as propylene, isobutene or tertiary butanol. The process comprises carrying out the ammoxidation such that the organic acid/unreacted ammonia ratio in an ammoxidation product gas is controlled to remain within the range from 0.8 to 3.0 inclusive in a reactor, introducing the ammoxidation product gas into a quench tower, and reacting in the tower the unreacted ammonia with the organic acid produced in a reactor, to fix the unreacted ammonia as an ammonium salt of the organic acid.

24 Claims, No Drawings

PROCESS FOR PRODUCING UNSATURATED NITRILE

This application is a 371 of PCT/JP96/00148 filed on Jan. 26, 1996.

TECHNICAL FIELD

The present invention relates to a process for producing an unsaturated nitrile, represented by acrylonitrile or methacrylonitrile, by ammoxidation.

BACKGROUND ART

A process for producing acrylonitrile or methacrylonitrile by bringing propylene, alternatively isobutene or tertiary butanol, into vapor-phase contact with a catalyst in the presence of ammonia and molecular oxygen is widely known as ammoxidation of an olefin and is practiced on an industrial scale at present. In this process, the molar ratio of ammonia to propylene in a reaction gas to be fed is usually set at 1.1 or more in order to increase the yield of the unsaturated nitrile, but the gas exhausted from a reactor contains a large amount of unreacted ammonia, owing to a disturbance of stoichiometric balance. A technique for treating the unreacted ammonia is an important problem from the viewpoint of the rationalization of the process, the prevention of environment pollution, etc., and various techniques have been developed in order to solve such a problem. For example, JP-B-49-25560, JP-B-51-49146, JP-A-52-4500, etc. disclose that the unreacted ammonia is separated and recovered as ammonium sulfate by the use of sulfuric acid. JP-B-51-3131 discloses that after the recovery of ammonia from the produced ammonium sulfate, the residual solution is incinerated. Deepwell injection of this waste solution is also carried out but the above-mentioned method associated with the use of sulfuric acid is not a preferable technique from the viewpoint of environmental pollution because SOx is generated when incinerating the produced ammonium sulfate.

On the other hand, as a method for treating the unreacted ammonia, JP-B-40-6451 and JP-A-52-32893 disclose the employment of an organic acid such as acetic acid, citric acid or an organic polybasic acid instead of sulfuric acid, and JP-B-45-33538 discloses the employment of carbonic acid gas. These methods permit treatment of the unreacted ammonia in the gas exhausted from the reactor, but they require the improvement and increase of facilities, etc., resulting in a complicated procedure, and moreover they are not economically advantageous.

As another method, i.e., a method in which substantially no unreacted ammonia is exhausted from the reactor, JP-A-7-53494, JP-A-7-126237 and JP-A-51-16615 disclose a method of supplying an organic compound to the reactor to reduce or substantially eliminate the unreacted ammonia. However, this method permits reduction or curtailment of the unreacted ammonia in the gas exhausted from the reactor but it requires further provision of other facilities in the reactor, resulting in complicated operations.

As yet another method for reducing or curtailing the unreacted ammonia in the gas exhausted from the reactor, JP-B-53-18014 discloses a method of carrying out the reaction while adjusting the molar ratio of ammonia to propylene in a reaction gas to be fed to a value near 1.0 by the use of a catalyst composed mainly of iron and antimony. It can be seen, however, from the results of analysis of the reaction product which are disclosed in this reference, that no acrylic acid was produced as a by-product.

JP-A-48-72122 discloses a method of regulating the ammonia concentration in a reaction gas to 0.8 vol % or less by adjusting the molar ratio of ammonia to propylene to 0.95–1.1 by the use of a catalyst containing as essential constituents molybdenum, bismuth, iron, cobalt, nickel, phosphorus and sodium. However, also in this method, the employment of sulfuric acid is indispensable for treating the unreacted ammonia.

JP-B-45-2371, JP-B-62-46538, JP-A-7-82228, etc. describe analytical values for acrylic acid in addition to the yield of acrylonitrile. JP-A-55-13187 describes analytical values for acrylic acid and unreacted ammonia in addition to the yield of acrylonitrile. However, none of these references mention the molar ratio of an organic acid to unreacted ammonia in an ammoxidation product gas and disclose that the unreacted ammonia is reacted with the organic acid (e.g. acrylic acid or acetic acid) produced by the ammoxidation, to be fixed as ammonium salt of the organic acid.

DISCLOSURE OF INVENTION

The present inventors earnestly investigated in order to solve the above problem, and consequently found a simple process for producing an unsaturated nitrile such as acrylonitrile or methacrylonitrile by ammoxidation of an organic compound such as propylene, alternatively isobutene or tertiary butanol, wherein unreacted ammonia is reacted with an organic acid produced by the ammoxidation, to be fixed as ammonium salt of the organic acid. Thus, the present invention has been accomplished.

The present invention is a process for production of an unsaturated nitrile such as acrylonitrile or methacrylonitrile by ammoxidation of an organic compound such as propylene, alternatively isobutene or tertiary butanol, which includes carrying out the ammoxidation while controlling the molar ratio of an organic acid present as a by-product in an ammoxidation product gas (hereinafter also referred to as "product gas") in a reactor to unreacted ammonia (hereinafter referred to as "organic acid/unreacted ammonia ratio") at 0.8–3.0, introducing the product gas into a quench tower, and reacting in the tower the unreacted ammonia with the organic acid produced in the reactor, to fix the unreacted ammonia as ammonium salt of the organic acid.

The present invention makes it possible to produce an unsaturated nitrile easily by fixing unreacted ammonia as an ammonium salt of an organic acid by a simple method not requiring complicated apparatus and operations. Moreover, the invention permits stable operation of a quench tower in spite of no use of sulfuric acid because a viscous and tarry substance is hardly produced. Furthermore, the invention has the following excellent effects: the invention causes no SOx production in the incineration of waste water because no ammonium sulfate is produced, hence has no undesirable influence on the environment, and also facilitates heat recovery, so that the rationalization of a waste water treating system becomes possible.

BEST MODE FOR CARRYING OUT THE INVENTION

In the present invention, the ammoxidation is effected while controlling the organic acid/unreacted ammonia ratio in an ammoxidation product gas at 0.8–3.0, preferably 0.9–2.0, more preferably 1.0–1.5.

For reacting the unreacted ammonia with the organic acid produced in the reactor to fix the same as ammonium salt of the organic acid in the quench tower, the organic acid/unreacted ammonia ratio in the quench tower is preferably controlled at 1.0 or more. Therefore, in the present invention, substantially the whole unreacted ammonia can be fixed with industrial advantage as an ammonium salt of the organic acid when an average (time average) obtained by dividing a value obtained by integrating the organic acid/ unreacted ammonia ratio in the product gas with respect to an axis referring to time by a reaction time is controlled at 1.0 or more in the ammoxidation.

Even if the organic acid/unreacted ammonia ratio is not less than 0.8 but less than 1.0, a substantial amount of the organic acid is present in the product gas, and a free organic acid, which is not reacted with ammonia, is also present in a circulating solution in the quench tower so that a large portion of the unreacted ammonia can be efficiently fixed. The residual unreacted ammonia can be fixed with industrial advantages, if necessary, by a conventional technique, for example, using a small amount of acetic acid, acrylic acid, citric acid, sulfuric acid or the like. The reaction can be carried out in a short period of time even if the organic acid/unreacted ammonia ratio is less than 0.8. However, this condition is not desirable since it possibly results in staining of a circulating solution in the quench tower because of polymerization of acrolein, which is an unsaturated aldehyde, or prussic acid and in reduced yield of acrylonitrile, which is an unsaturated nitrile, because of production of succinonitrile, etc. depending upon the efficiency of contact in the quench tower between the product gas and the circulating solution.

The reason why the organic acid/unreacted ammonia ratio in the product gas is controlled at a value in the above range is that in the ammoxidation in industrial-scale, there is a fear of, for example, the following troubles: the ratio of the organic acid to ammonia in a circulating solution in the quench tower changes for some cause, resulting in insufficient fixation of the unreacted ammonia, or the organic acid is present in excess.

When the time average of the organic acid/unreacted ammonia ratio in the product gas tends to decrease at a point of time, reducing the molar ratio of ammonia to propylene in a starting gas to a value lower than the value at the point of time increases the organic acid/unreacted ammonia ratio in the reaction product gas, so that the time average of the organic acid/unreacted ammonia ratio can be increased. In contrast, when the time average of the organic acid/ unreacted ammonia ratio in the ammoxidation product gas tends to increase at a point of time, increasing the molar ratio of ammonia to propylene in the starting gas to a value higher than the value at the point of time reduces the organic acid/unreacted ammonia ratio in the product gas, so that the time average of the organic acid/unreacted ammonia ratio can be reduced.

Thus, the unreacted ammonia can be fixed with industrial advantage by controlling the time average of the organic acid/unreacted ammonia ratio in the production gas in a given range during the ammoxidation.

Substantially, the ratio of the organic acid to ammonia in the circulating solution in the quench tower correlates with the pH value of the circulating solution. Therefore, the above-mentioned control of the organic acid/unreacted ammonia ratio can be carried out by determining reaction conditions such as the molar ratio of ammonia to propylene in the starting gas, depending on the change of the pH value of the circulating solution in the quench tower.

For example, when the ratio or the organic acid to ammonia in the circulating solution in the quench tower is desired to be rapidly changed, or in an urgent need to control the reaction, it is also possible to supply an organic acid (e.g. acetic acid or acrylic acid) or a base (e.g. ammonia or an amine) to the circulating solution. In the present invention, sulfuric acid need not be used at all or substantially.

The organic acid in the present invention includes acrylic acid, acetic acid, methacrylic acid, etc., which are produced by the ammoxidation. The unreacted ammonia is ammonia substantially present in the product gas exhausted from the reactor.

In the case where the ammoxidation is continued under conditions outside the range specified in the present invention, for example, at an organic acid/unreacted ammonia ratio in the product gas of less than 0.8, the yield of the unsaturated nitrile is high but polymers of acrolein, which is an unsaturated aldehyde, and prussic acid are produced in the quench tower in the next step, resulting in not only markedly deteriorated quality of the circulating solution, but also disadvantages such as a loss of acrylonitrile caused by the production of succinonitrile. When the ammoxidation is continued at an organic acid/unreacted ammonia ratio of more than 3.0, the yield of the unsaturated nitrile is decreased and moreover the amount of unsaturated aldehydes (e.g. acrolein) and high-boiling compounds is increased in the product gas, resulting in problems such as contamination of the circulating solution in the quench tower with tarry substances and staining of a heat exchanger provided at the outlet of the reactor.

As to a method for controlling the organic acid/unreacted ammonia ratio to a value within the range specified in the present invention, the control can be carried out by properly choosing the molar ratio of ammonia to propylene, the molar ratio of ammonia to isobutene or the molar ratio of ammonia to tertiary butanol in a starting gas to be fed to the reactor, in a range of 0.90–1.20, preferably 0.95–1.10, depending on reaction conditions such as the catalytic activity, catalyst amount, reaction temperature, reaction pressure, etc.

The ammoxidation product gas exhausted from the reactor is introduced into the quench tower, where the unreacted ammonia is reacted with the organic acid produced by the ammoxidation to be fixed as ammonium salt of the organic acid.

As the quench tower used in the present invention, there may be used either a quench tower composed of a single compartment or a multi-stage quench tower divided into at least two compartments, an upper compartment and a lower compartment. The multi-stage quench tower is preferably used.

In the case of using the multi-stage quench tower, the reaction gas coming out of the reactor is introduced into the lower compartment of the quench tower where the reaction gas is brought into contact with a circulating solution containing ammoxidation products such as ammonium salt of the organic acid, high-boiling compounds, etc., whereby the organic acid and the unreacted ammonia in the reaction gas are fixed as ammonium salt of the organic acid in the circulating solution. At the same time, the high-boiling compounds and products by polymerization of acrylonitrile, acrolein, prussic acid, etc., which are produced during the ammoxidation, the scattered catalyst and the like are also separated and removed. In addition, the reaction gas is introduced into the upper compartment and then the fixation of the unreacted ammonia is completed by the same procedure as above. The circulating solution in the quench tower is recycled in direct contact with the reaction gas. As to the operation of the quench tower, examples of a method for making up a water deficiency caused by evaporation in the lower compartment include using a liquid formed by condensation in the upper compartment supplying water from the outside and the like. The method of using a liquid formed by condensation in the upper compartment is preferable for reducing the amount of waste water to be treated. As the solution temperature in the lower compartment of the quench tower, any temperature may be employed so long as it is 100° C. or less, though the solution temperature is preferably 50–95° C., more preferably 60–90° C. from the viewpoint of the degree of concentration of the waste water, the decomposition temperature of the ammonium salt of the organic acid, etc.

Since the solution taken out of the quench tower (hereinafter referred to as "taken-out solution") in the present invention contains, besides the ammonium salt of the organic acid, high-boiling compounds produced by the ammoxidation and heavier components formed by the polymerization of acrylonitrile, acrolein, prussic acid, etc. but not sulfuric acid, it can easily be concentrated and can be incinerated. In the concentration, the degree of concentration of the taken-out solution can be determined from the viewpoint of difficulty in handling due to self-burning properties and a viscosity increase and from an economical viewpoint.

The degree of concentration is determined so that heavier components may be 10 to 70 wt %, preferably 40 to 60 wt %. It is also preferable to separate a solid component composed mainly of catalyst particles, metal components, etc. from the taken-out solution before the concentration or the incineration.

The concentration of the heavier components is determined by weighing the taken-out solution into an evaporating dish, heating the solution on a 100° C. water bath, drying the solution in a drying oven at 105° C., and then measuring the weight of the residue.

For incinerating the taken-out solution from the quench tower, the solution may be fed to an incinerator directly from the quench tower or after being stored in a storage tank. The storage tank and piping therefrom to the incinerator are preferably kept hot for preventing clogging.

Equipment for incinerating the taken-out solution is not particularly limited and there can be used, for example, an ordinary spray-incineration type incinerator or a fluidized-bed incinerator. The taken-out solution can be incinerated together with waste gas in a waste gas incinerator intended for incinerating this waste gas exhausted from an absorption tower in the ammoxidation process. As a spraying method, there can be employed, for example, a self-pressurizing spraying method using a high pressure and a two-fluid nozzle method using steam or high-pressure air as an atomizing source. There is preferably employed the two-fluid nozzle method using steam as an atomizing source which permits satisfactory spraying.

For the incineration, fuel oil, prussic acid produced as a by-product by the ammoxidation, etc. may be used as an auxiliary fuel.

Although the inside temperature of the incinerator is varied depending on the composition of the taken-out solution which is to be incinerated, a combustion method employed in the incinerator, the residence time of incineration gas in the incinerator, the oxygen concentration in exhaust gas from the incinerator, etc., it is 500–1,300° C., preferably 650–850° C. The residence time of incineration gas in the incinerator is 0.5 to 5 seconds, preferably 1 to 3 seconds. The oxygen concentration in exhaust gas from the incinerator is 0.5 to 5 vol %, preferably 1 to 3 vol %.

Heat generated by the incineration can be recovered by means of a heat exchanger, a heat exchanger coil or the like.

Since no SOx is produced because no sulfuric acid is used, the process for producing unsaturated nitrile of in the present invention is advantageous also from the viewpoint of the protection of the environment.

In the present invention, acrylonitrile or methacrylonitrile is produced by ammoxidation of propylene, isobutene or tertiary butanol. The ammoxidation is preferably carried out in a fluidized bed by using an oxide catalyst comprising 30 to 70 wt % of silica and 70 to 30 wt % of molybdenum, bismuth and iron supported on the silica. As the oxide catalyst in the present invention, there is more preferably used a catalyst represented by the general formula:

$$Mo_y Bi_p Fe_q A_a B_b C_c D_d O_f$$

, wherein Mo is molybdenum, Bi is bismuth, Fe is iron, A is at least one element selected from the group consisting of nickel and cobalt, B is at least one element selected from the group consisting of potassium, rubidium and cesium, C is at least one element selected from the group consisting of magnesium and zinc, D is at least one element selected from rare earth elements, O is oxygen, y, p, q, a, b, c, d and f are atomic ratio values of molybdenum, bismuth, iron, A, B, C, D and oxygen, respectively, d/(p+d)=0.6 to 0.8, p+d=0.5 to 2, q=0.1 to 3, a=4 to 10, b=0.01 to 2, c=0 to 3, f being the number of oxygen atoms necessary for satisfying the valence requirements of the other elements present in the catalyst, in which the atomic ratio value y of molybdenum is in a range of y=1.02x to 1.10x wherein x is defined by the equation x=1.5p+q+a+c+1.5d.

In the above-mentioned oxide catalyst, A is preferably nickel. D is preferably at least one element selected from the group consisting of yttrium, lanthanum, cerium, praseodymium, neodymium and samarium, more preferably cerium.

The atomic ratio value y of molybdenum is preferably used in a range of y=1.04x to 1.08x. The atomic ratio value y of molybdenum can be kept in the above range, for example, by adding a molybdenum oxide represented by the general formula $Mo_x O_y$ wherein the Y/X ratio is 1–3 (e.g. $MoO_3$, $MoO_2$, $Mo_2O_3$, $Mo_2O_5$, $Mo_3O_8$, $Mo_4O_{11}$, $Mo_8O_{23}$ or $Mo_9O_{26}$), a molybdenum compound convertible to molybdenum oxide under the reaction conditions, for example, a molybdic acid (e.g. $H_2MoO_4$ or $H_2MoO_4.H_2O$), an ammonium salt of molybdic acid (e.g. $(NH_4)_2MoO_4$ or $(NH_4)_6Mo_7O_{24}.4H_2O$), a molybdenum sulfide (e.g. $MOS_3$ or $MOS_2$), a halogenated molybdenum (e.g. $MoOCl_4$, $MoO_2Cl_3$, $MoOCl_3$, $MoCl_5$ or $MoCl_4$), a carbonyl compound of molybdenum (e.g. $Mo(CO)_6$, $(C_5H_5)Mo(CO)_5Mo(C_5H_5)$, $(C_5H_5)Mo(CO)_3H$, $Mo(CO)_3(C_5H_5N)_3$ or $Mo_2(CO)_6(H_2NCH_2CH_2NH_2)_3$), or a cyano compound of molybdenum (e.g. $H_4[Mo(CN)_7(OH)_2]$); or a catalyst having the same composition except for an increased proportion of molybdenum.

The above-mentioned oxide catalyst can be obtained by a well-known method, for example, by compounding starting materials for individual metal components to prepare a solution, spray-drying the thus prepared solutions to obtain a dried product, and calcining the dried product finally. In compounding the starting materials, there are preferably used silica sol for silica, a ammonium salt of molybdenum for molybdenum, and water-soluble compounds such as nitrates for the other components. For atomization in the spray-drying of the starting solutions, a centrifugal method is preferable. The drying temperature is 100–400° C., preferably 150–300° C. The calcination of the dried product is carried out in a temperature range of 500–750° C., preferably 550–700° C., for 1 to 20 hours, if necessary, after pre-calcination carried out at 150–500° C.

The organic compound used in the ammoxidtion in the present invention includes propylene, isobutene and tertiary butanol. When propylene is used as the organic compound, acrylonitrile is produced as the unsaturated nitrile, and when isobutene and/or tertiary butanol is used as the organic compound, methacrylonitrile is produced as the unsaturted nitrile.

The above-mentioned organic compound and ammonia, starting materials, need not be of high purity and may be of industrial grade.

As an oxygen source, air is usually preferable, though there may be used a gas with an increased oxygen concentration prepared, for example, by mixing oxygen with air.

As to conditions for the ammoxidation, the composition of a starting gas is such that molar ratios of an organic compound (e.g. propylene, isobutene or tertiary butanol), ammonia and air is as follows: organic compound/ammonia/air=1/0.90–1.20/8–10, preferably 1/0.95–1.10/8–10. The reaction temperature is 400–460° C., particularly preferably 415–445° C. The reaction pressure is in a range of atmospheric pressure to 3 atm. The contact time of the starting gas with the catalyst is 0.5 to 20 sec·g/ml, preferably 1 to 10 sec·g/ml.

The present invention is illustrated below in further detail with reference to examples.

A reaction apparatus was composed of a fluidized reactor with a diameter of 3 inches having 16-mesh wire gauzes provided therein at intervals of 1 cm, a quench tank with a diameter of 4 inches and a height of 400 mm, and connecting piping. A reaction gas from the reactor was introduced into the quench tank through ½-inch piping heated and maintained at 200–250° C., and bubbled into a liquid in the quench tank through a nozzle having 10 holes of 3 mmφ. The quench tank was provided with a sight-glass type level gage designed to show the volume of the quench liquid and the situation in the tank, a temperature controller for controlling the temperature of the quench liquid, an electric heater, and a temperature maintenance apparatus. In addition, the quench tank was equipped with piping for sampling the quench liquid and piping for exhausting waste gas. The temperature of the liquid in the quench tank was controlled by heating with the heater setting the temperature controller at 70° C. to attain conditions under which substantially the same effect as in a quench tower can be obtained. The liquid in the quench tank was sampled by a batch method. That is, the liquid was sampled at intervals of about 5 hours so as to adjust the liquid level in the quench tank to a definite level, and the quality of the quench liquid was checked and the inside of the quench tank was observed through the sight glass of the tank. The reaction pressure P was regulated to 0.5 kg/cm²G by attaching a regulating valve to the exhaust piping of the quench tank.

The reaction results were analyzed by a titration method by taking out a part of the reaction gas from the piping connecting the reactor and the quench tank, followed by gas chromatography and an absorption procedure. All of materials for the apparatus, the piping, etc. were stainless steel (SUS304).

The amount W of catalyst charged was 1,000 to 2,000 g, and the total gas feed rate F was 100 to 150 ml/sec (in terms of a rate at NTP).

The contact time is defined by the following equation:

$$\text{Contact time (sec·g/ml)} = (W/F) \times 273/(273+T) \times (103+P)/1.03$$

wherein W is the amount of the catalyst F is the gas feed rate, T is the reaction temperature and P is the reaction pressure.

The conversion and yields used to express the reaction results in the working and comparative examples are defined by the following equations:

Conversion (%)=[(number of moles of reacted propylene)/(number of moles of fed propylene)×100]

Acrylonitrile yield (%)=[(number of moles of produced acrylonitrile)/(number of moles of fed propylene)×100]

Acrolein yield (%)=[(number of moles of produced acrolein)/(number of moles of fed propylene)×100]

Acrylic acid yield (%)=[(number of moles of produced acrylic acid)/(number of moles of fed propylene)×100]

Acetic acid yield (%)=[(number of moles of produced acetic acid× ⅔)/(number of moles of fed propylene)×100]

Unreacted ammonia percentage (%)=[(number of moles of ammonia determined by titration+number of moles of acrylic acid+number of moles of acetic acid)/(number of moles of fed propylene)×100]

The measurement of unreacted ammonia by titration was carried out in the following manner: a 1/10 N aqueous nitric acid solution was allowed to absorb a predetermined amount of a gas collected at the outlet of the reactor, and there was taken as an end point the point at which the solution changed in color from yellow to blue when titrated with a 1/10 aqueous sodium hydroxide solution by the use of Bromocresol Green as an indicator.

In operating the reactor, the molar ratio of propylene to air was adjusted to a value properly chosen in a range of propylene/air=1/8+010, for adjusting the oxygen concentration in a gas present at the outlet of the reactor to 0.01 to 0.20 vol %.

EXAMPLE 1

Present Invention

A catalyst composed of 50 wt % of silica and an oxide with a composition of $Mo_{11.7}Bi_{0.20}Ce_{0.40}Fe_{2.0}Ni_{5.6}Mg_{2.2}K_{0.07}Cs_{0.04}$ supported on the silica was prepared as follows.

Added to 3333.3 g of silica sol containing 30 wt % of $SiO_2$ was a solution prepared by dissolving in 755.6 g of 17.9 wt % nitric acid 39.2 g of bismuth nitrate $[Bi(NO_3)_3.5H_2O]$, 70.3 g of cerium nitrate $[Ce(NO_3)_3.6H_2O]$, 326.9 g of iron nitrate $[Fe(NO_3)_3.9H_2O]$, 658.8 g of nickel nitrate $[Ni(NO_3)_2.6H_2O]$, 228.1 g of magnesium nitrate $[Mg(NO_3)_2.6H_2O]$, 2.86 g of potassium nitrate $[KNO_3]$ and 3.15 g of cesium nitrate $[CsNO_3]$. Finally, a solution of 835.7 g of ammonium paramolybdate $[(NH_4)_6Mo_7O_{24}.4H_2O]$ in 1671.4 g of water was added.

The starting solution thus prepared was fed to a parallel-flow type spray dryer and granulated and dried at about 200° C. The atomization of said solution was carried out with an atomizer equipped with a dished rotor and provided in the upper part of the dryer. The resulting granulated powder was pre-calcined at 400° C. for 1 hour in an electric oven and then calcined at 590° C. for 2 hours to obtain the catalyst.

Using 1400 g of the catalyst obtained, ammoxidation of propylene was carried out at a reaction temperature of 430° C. and a contact time of 6.0 sec·g/ml, and at around an ammonia/propylene mole ratio of 1.02 so that the organic acid/unreacted ammonia ratio might be kept at a value of 1.2. One week after the initiation of the reaction, the conversion was 99.8%, the acrylonitrile yield 79.8%, the acrolein yield 1.3%, the acrylic acid yield 2.1%, the acetic acid yield 0.1%, the unreacted ammonia percentage 1.9%, and the organic acid/unreacted ammonia ratio 1.2. A sample of the quench liquid was light-yellow and contained no tarry and viscous substances. Neither suspended matter nor a tarry substance was found by observation through the sight glass of the quench tank.

When the reaction was continued for another 2 weeks under the above-mentioned conditions, substantially the same reaction results as above were obtained, and the quench liquid was light-yellow and contained no tarry and viscous substances. In addition, neither suspended matter nor a tarry substance was found by observation through the sight glass of the quench tank. During the reaction thus continued for 3 weeks in total, the reaction apparatus could be satisfactorily operated without clogging of very thin piping for analysis and the piping of the quench tank. After termination of the reaction, the quench tank was opened and its inside was inspected to find no tarry and viscous substances.

When 1 liter of the liquid taken out of the quench tank in the present example was placed on an evaporating dish and concentrated to dryness on a water bath at 100° C., about 160 g of nonvolatile matter remained. In addition, when incinerated in an electric oven at 800° C., the nonvolatile matter could be completely incinerated, leaving substantially no solid residue. Since no sulfuric acid was used, no sulfur oxide (SOx) was present in waste gas produced by the incineration.

EXAMPLE 2

Present Invention

A catalyst with a composition of $Mo_{11.7}Bi_{0.45}Ce_{0.90}Fe_{1.8}Ni_{5.0}Mg_{2.0}K_{0.09}Rb_{0.05}$ supported on silica (50 wt %) was prepared in the same manner as in Example 1 except for changing the calcination temperature to 610° C.

Using 1400 g of the catalyst obtained, ammoxidation of propylene was carried out at a reaction temperature of 430° C. and a contact time of 6.7 sec·g/ml, and at around an ammonia/propylene mole ratio of 1.03 so that the organic acid/unreacted ammonia ratio might be kept at a value of 1.0. One week after the initiation of the reaction, the conversion was 99.8%, the acrylonitrile yield 80.9%, the acrolein yield 1.2%, the acrylic acid yield 2.0%, the acetic acid yield 0.1%, the unreacted ammonia percentage 2.1%, and the organic acid/unreacted ammonia ratio 1.0. A sample of the quench liquid was light-yellow and contained no tarry and viscous substances. Neither suspended matter nor a tarry substance was found by observation through the sight glass of the quench tank.

When the reaction was continued for another 2 weeks under the above-mentioned conditions, substantially the same reaction results as above were obtained, and the quench liquid was light-yellow and contained no tarry and viscous substances. In addition, neither suspended matter nor a tarry substance was found by observation through the sight glass of the quench tank. During the reaction thus continued for 3 weeks in total, the reaction apparatus could be satisfactorily operated without clogging of the very thin piping for analysis and the piping of the quench tank. After termination of the reaction, the quench tank was opened and its inside was inspected to find no tarry and viscous substances.

When 1 liter of the liquid taken out of the quench tank in the present example was placed on an evaporating dish and concentrated to dryness on a water bath at 100° C., about 150 g of nonvolatile matter remained. In addition, when incinerated in an electric oven at 800° C., the nonvolatile matter could be completely incinerated, leaving substantially no solid residue. Since no sulfuric acid was used, no sulfur oxide (SOx) was present in waste gas produced by the incineration.

EXAMPLE 3

Present Invention

A catalyst with a composition of $Mo_{11.8}Bi_{0.60}Ce_{1.20}Fe_{1.6}Ni_{4.8}Mg_{1.9}K_{0.11}Rb_{0.05}$ supported on silica (50 wt %) was prepared by calcination at 590° C. in the same manner as in Example 1.

Using 1400 g of the catalyst obtained, ammoxidation of propylene was carried out at a reaction temperature of 430° C. and a contact time of 6.2 sec·g/ml, and at around an ammonia/propylene mole ratio of 1.02 so that the organic acid/unreacted ammonia ratio might be kept at a value of 1.2. One week after the initiation of the reaction, the conversion was 99.8%, the acrylonitrile yield 80.4%, the acrolein yield 1.2%, the acrylic acid yield 2.2%, the acetic acid yield 0.1%, the unreacted ammonia percentage 2.0%, and the organic acid/unreacted ammonia ratio 1.2. A sample of the quench liquid was light-yellow and contained no tarry and viscous substances. Neither suspended matter nor a tarry substance was found by observation through the sight glass of the quench tank.

When the reaction was continued for another 2 weeks under the above-mentioned conditions, substantially the same reaction results as above were obtained, and the quench liquid was light-yellow and contained no tarry and viscous substances. In addition, neither suspended matter nor a tarry substance was found by observation through the sight glass of the quench tank. During the reaction thus continued for 3 weeks in total, the reaction apparatus could be satisfactorily operated without clogging of the very thin piping for analysis and the piping of the quench tank. After termination of the reaction, the quench tank was opened and its inside was inspected to find no tarry and viscous substances.

When 1 liter of the liquid taken out of the quench tank in the present example was placed on an evaporating dish and concentrated to dryness on a water bath at 100° C., about 170 g of nonvolatile matter remained. In addition, when incinerated in an electric oven at 800° C., the nonvolatile matter could be completely incinerated, leaving substantially no solid residue. Since no sulfuric acid was used, no sulfur oxide (SOx) was present in waste gas produced by the incineration.

EXAMPLE 4

Present Invention

A catalyst with a composition of $Mo_{11.7}Bi_{0.30}Pr_{0.13}Nd_{0.47}Fe_{2.0}Ni_{5.4}Mg_{2.1}K_{0.09}Rb_{0.05}$ supported on silica (50 wt %) was prepared by calcination at 590° C. in the same manner as in Example 1.

Using 1400 g of the catalyst obtained, ammoxidation of propylene was carried out at a reaction temperature of 430° C. and a contact time of 6.7 sec·g/ml, and at around an ammonia/propylene mole ratio of 1.02 so that the organic acid/unreacted ammonia ratio might be kept at a value of 1.1. One week after the initiation of the reaction, the conversion was 99.8%, the acrylonitrile yield 80.3%, the acrolein yield 1.3%, the acrylic acid yield 2.1%, the acetic acid yield 0.1%, the unreacted ammonia percentage 2.1%, and the organic acid/unreacted ammonia ratio 1.1. A sample of the quench liquid was light-yellow and contained no tarry and viscous substances. Neither suspended matter nor a tarry substance was found by observation through the sight glass of the quench tank.

When the reaction was continued for another 2 weeks under the above-mentioned conditions, substantially the same reaction results as above were obtained, and the quench liquid was light-yellow and contained no tarry and viscous substances. In addition, neither suspended matter nor a tarry substance was found by observation through the sight glass of the quench tank. During the reaction thus continued for 3 weeks in total, the reaction apparatus could be satisfactorily operated without clogging of the very thin piping for analysis and the piping of the quench tank. After termination of the reaction, the quench tank was opened and its inside was inspected to find no tarry and viscous substances.

When 1 liter of the liquid taken out of the quench tank in the present example was placed on an evaporating dish and concentrated to dryness on a water bath at 100° C., about 180 g of nonvolatile matter remained. In addition, when incinerated in an electric oven at 800° C., the nonvolatile matter could be completely incinerated, leaving substantially no solid residue. Since no sulfuric acid was used, no sulfur oxide (SOx) was present in a waste gas produced by the incineration.

EXAMPLE 5

Comparison

The same operation as in Example 1 was carried out using the same catalyst as used in Example 1, except for changing the ammonia/propylene mole ratio to around 0.94 so that the organic acid/unreacted ammonia ratio might be kept at a value of 3.3. Three days after the initiation of the reaction, the conversion was 99.8%, the acrylonitrile yield 76.3%, the acrolein yield 2.8%, the acrylic acid yield 2.5%, the acetic acid yield 0.1%, the unreacted ammonia percentage 0.8%, and the organic acid/unreacted ammonia ratio 3.3. A sample of the quench liquid was brown and contained suspended matter and a tarry substance which were regarded as polymers of acrolein and acrylic acid. Moreover, the piping (inside diameter: 3 mm) for analysis was clogged with a tarry and viscous substance. The operation was judged to be difficult to continue under the same conditions, so that the reaction was stopped on the fifth day after the initiation of the reaction.

EXAMPLE 6

Comparison

The same operation as in Example 1 was carried out using the same catalyst as used in Example 1, except for changing the ammonia/propylene mole ratio to around 1.10 so that the organic acid/unreacted ammonia ratio might be kept at a value of 0.2. One week after the initiation of the reaction, the conversion was 99.7%, the acrylonitrile yield 83.0%, the acrolein yield 0.3%, the acrylic acid yield 1.2%, the acetic acid yield 0.1%, the unreacted ammonia percentage 6.0%, and the organic acid/unreacted ammonia ratio 0.2. A sample of the quench liquid was brownish black and contained black suspended matter and a black precipitate which were regarded as polymers of prussic acid and acrylonitrile.

In this condition, the operation of the quench tank was difficult to continue, and the addition of an acid such as sulfuric acid was necessary.

EXAMPLE 7

Present Invention

Using 1400 g of the catalyst obtained in Example 1, ammoxidation of propylene was carried out, over three days, at a reaction temperature of 430° C. and a contact time of 6.0 sec·g/ml, alternately for 4 hours at around an ammonia/propylene mole ratio of 1.01 so that the organic acid/unreacted ammonia ratio might be kept at a value of 1.3, and for 2 hours at around an ammonia/propylene mole ratio of 1.05 so that the organic acid/unreacted ammonia ratio might be kept at a value of 0.8. A sample of the quench liquid taken out during the ammoxidation was yellow and contained no tarry and viscous substances, and the ammoxidation could be carried out with no trouble. After termination of the reaction, the quench tank was opened and its inside was inspected to find no tarry and viscous substances.

Under the former reaction conditions, the conversion was 99.8%, the acrylonitrile yield 79.4%, the acrolein yield 1.5%, the acrylic acid yield 2.2%, the acetic acid yield 0.1%, the unreacted ammonia percentage 1.8%, and the organic acid/unreacted ammonia 1.3, while under the latter reaction conditions, the conversion was 99.8%, the acrylonitrile yield 81.2%, the acrolein yield 0.9%, the acrylic acid yield 1.8%, the acetic acid yield 0.1%, the unreacted ammonia percentage 2.4%, and the organic acid/unreacted ammonia ratio 0.8. Thus, the time average over 6 hours of the organic acid/unreacted ammonia ratio in the present ammoxidation was 1.1.

When 1 liter of the liquid taken out of the quench tank in the present example was placed on an evaporating dish and concentrated to dryness on a water bath at 100° C., about 220 g of nonvolatile matter remained. In addition, when incinerated in an electric oven at 800° C., the nonvolatile matter could be completely incinerated, leaving substantially no solid residue. Since no sulfuric acid was used, no sulfur oxide (SOx) was present in waste gas produced by the incineration.

INDUSTRIAL APPLICABILITY

The present invention makes it possible to produce an unsaturated nitrile by fixing unreacted ammonia as an ammonium salt of an organic acid by a simple method not requiring complicated apparatus and operations. Moreover, the invention permits stable operation of a quench tower in spite of no use of sulfuric acid because a tarry and viscous substance is hardly produced. Furthermore, the invention causes no SOx production in the incineration of waste water because no ammonium sulfate is produced, hence has no undesirable influence on the environment, and also facilitates heat recovery, so that the rationalization of a waste water treating system becomes possible.

What is claimed is:

1. A process for producing an unsaturated nitrile by ammoxidation of an organic compound, which comprises
   carrying out the ammoxidation in a fluidized bed with an oxide catalyst comprising from 70 to 30 wt % of the sum of the elements molybdenum, bismuth and iron and a support comprising from 30 to 70 wt % of silica
   such that the time-average of the molar ratio of an organic acid present as a by-product in an ammoxidation product gas (hereinafter referred to as "product gas") to unreacted ammonia (hereinafter referred to as "organic acid/unreacted ammonia ratio") is controlled to remain within the range from 0.8 to 3.0 inclusive in a reactor, said oxide catalyst being represented by the general formula:

$$Mo_y Bi_p Fe_q A_a B_b C_c D_d O_f,$$

wherein Mo is molybdenum, Bi is bismuth, Fe is iron, A is at least one element selected from the group consisting of nickel and cobalt, B is at least one element selected from the group consisting of potassium, rubidium and cesium, C is at least one selected from the group consisting of magnesium and zinc, D is at least one element selected from rare earth elements, O is oxygen, y, p, q, a, b, c, d and f are atomic ratio values of molybdenum, bismuth, iron, A, B, C, D and oxygen, respectively, d/(p+d)=0.6 to 0.8, p+d=0.5 to 2.0, q=0.1 to 3, a=4 to 10, b=0.01 to 2, c=0 to 3, f being the number of oxygen atoms necessary for satisfying the valence requirements of the other elements present in said oxide catalyst, in which the atomic ratio value y of molybdenum of said oxide catalyst is in a range of y=1.02x to 1.10x wherein x is defined by the equation x=1.5p+q+a+c+1.5d, introducing said product gas into a quench tower, and reacting in the tower the unreacted ammonia with the organic acid produced in the reactor, to fix the unreacted ammonia as an ammonium salt of the organic acid.

2. The process according to claim 1, wherein said organic compound is at least one selected from the group consisting of propylene, isobutene and tertiary butanol and said unsaturated nitrile is acrylonitrile and/or methacrylonitrile which corresponds to said organic compound.

3. The process according to claim 1, wherein said organic compound is propylene and said unsaturated nitrile is acrylonitrile.

4. The process according to claim 1, wherein said organic compound is isobutene and/or tertiary butanol and said unsaturated nitrile is methacrylonitrile.

5. The process according to claims 1 or 3, which further comprises incinerating a liquid taken out of the quench tower and containing the ammonium salt of the organic acid.

6. The process according to claim 5, wherein vapor is recovered by heat exchange in the incineration of the liquid taken out of the quench tower.

7. The process according to claims 1 or 3, wherein the ammoxidation is carried out such that the time average of the organic acid/unreacted ammonia ratio is controlled to remain within the range from 0.9 to 2.0, inclusive.

8. The process according to claim 7, which further comprises incinerating a liquid taken out of the quench tower and containing the ammonium salt of the organic acid.

9. The process according to claim 8, wherein vapor is recovered by heat exchange in the incineration of the liquid taken out of the quench tower.

10. The process according to claims 1 or 3, wherein the ammoxidation is carried out such that the time average of the organic acid/unreacted ammonia ratio is controlled to remain within the range from 1.0 to 1.5, inclusive.

11. The process according to claim 10, which further comprises incinerating a liquid taken out of the quench tower and containing the ammonium salt of the organic acid.

12. The process according to claim 11, wherein vapor is recovered by heat exchange in the incineration of the liquid taken out of the quench tower.

13. The process according to claim 1, wherein substantially no acid is added to the quench tower from outside.

14. The process according to claim 13, wherein said organic compound is at least one selected from the group consisting of propylene, isobutene and tertiary butanol and said unsaturated nitrite is acrylonitrile and/or methacrylonitrile which corresponds to said organic compound.

15. The process according to claim 13, wherein said organic compound is propylene and said unsaturated nitrile is acrylonitrile.

16. The process according to claim 13, wherein said organic compound is isobutene and/or tertiary butanol and said unsaturated nitrile is methacrylonitrile.

17. The process according to claims 13 or 15, which further comprises incinerating a liquid taken out of the quench tower and containing the ammonium salt of the organic acid.

18. The process according to claim 17, wherein vapor is recovered by heat exchange in the incineration of the liquid taken out of the quench tower.

19. The process according to claims 13 or 15, wherein the ammoxidation is carried out such that the time average of the organic acid/unreacted ammonia ratio is controlled to remain within the range from 0.9 to 2.0, inclusive.

20. The process according to claim 19, which further comprises incinerating a liquid taken out of the quench tower and containing the ammonium salt of the organic acid.

21. The process according to claim 20, wherein vapor is recovered by heat exchange in the incineration of the liquid taken out of the quench tower.

22. The process according to claims 13 or 15, wherein the ammoxidation is carried out such that the time average of the organic acid/unreacted ammonia ratio is controlled to remain within the range from 1.0 to 1.5, inclusive.

23. The process according to claim 22, which further comprises incinerating a liquid taken out of the quench tower and containing the ammonium salt of the organic acid.

24. The process according to claim 23, wherein vapor is recovered by heat exchange in the incineration of the liquid taken out of the quench tower.

* * * * *